United States Patent [19]

Snyder

[11] Patent Number: 4,908,305
[45] Date of Patent: Mar. 13, 1990

[54] COMPETITIVE ELISA FOR DETERMINATION OF NEUTRALIZING IBDV ANTIBODY

[75] Inventor: David B. Snyder, Seabrook, Md.

[73] Assignee: The University of Maryland, College Park, Md.

[21] Appl. No.: 110,738

[22] Filed: Oct. 21, 1987

Related U.S. Application Data

[63] Continuation-in-part of Ser. No. 61,083, Jun. 12, 1987.

[51] Int. Cl.$^4$ .................. G01N 33/53; G01N 33/577; C07K 15/14; C12N 1/00
[52] U.S. Cl. ..................... 435/5; 424/85.8; 435/7; 435/810; 436/518; 436/538; 436/543; 436/548; 436/808; 436/811; 935/110
[58] Field of Search ............ 435/5, 7, 28, 68, 810, 435/172.2, 240.27; 436/506, 536, 538, 543, 548, 808, 819; 530/387; 424/85, 89, 85.8; 935/110, 104

[56] References Cited

U.S. PATENT DOCUMENTS

| | | | |
|---|---|---|---|
| 4,160,024 | 7/1979 | Schat et al. | 435/237 |
| 4,503,143 | 3/1985 | Gerber et al. | 436/510 |
| 4,530,831 | 7/1985 | Lütticken et al. | 435/235 |
| 4,535,057 | 8/1985 | Dreesman et al. | 436/513 |
| 4,559,229 | 12/1985 | Page et al. | 435/235 |
| 4,619,896 | 10/1986 | Shattock et al. | 436/528 |
| 4,661,445 | 4/1987 | Saxinger et al. | 436/808 |
| 4,689,224 | 8/1987 | Bull et al. | 424/88 |
| 4,783,399 | 11/1988 | Oldstone et al. | 436/548 |

OTHER PUBLICATIONS

Azad et al., Virology, vol. 149, pp. 190–198, 1986.
Snyder et al., Biological Abstracts, vol. 78(3), Abstract No. 19508, 1984, Avian Disease, vol. 28(1), 1984, pp. 12–24.
Cho et al., Biological Abstracts, vol. 84, Abstract No. 120283, 1987.
Yolken, Reviews of Infectious Disease, vol. 4, No. 1, pp. 35–68, 1982.
Mallinson et al. Poult. Sci., vol. 64(9), pp. 1661–1669, 1985.
Snyder et al., Biological Abstracts, vol. 82(3), Abstract No. 23798, 1986, Avian Disease, vol.30(1), 1986, pp. 139–148.

*Primary Examiner*—Esther M. Kepplinger
*Assistant Examiner*—Florina B. Hoffer
*Attorney, Agent, or Firm*—Oblon, Spivak, McClelland, Maier & Neustadt

[57] ABSTRACT

A method for determining the level of infectious bursal disease virus IBDV neutralizing antibody in poultry comprising a labeled monoclonal antibody R63 having the IBDV neutralizing capability of the monoclonal antibody expressed by hybridoma cell line ATCC HB-9490. Monoclonal antibody R63 is specific to all known IBDV strains and serotypes and competes only with itself and other antibodies recognizing the same neutralizing epitope present in poultry sera. In a competition assay, the increase in unbound labeled monoclonal antibody is an indication of the level of IBDV neutralizing antibody present in poultry sera.

9 Claims, No Drawings

COMPETITIVE ELISA FOR DETERMINATION OF NEUTRALIZING IBDV ANTIBODY

This application is a continuation-in-part of Application Ser. No. 07/061,083 filed June 12, 1987. The entire contents thereof are incorporated herein, by reference.

BACKGROUND OF THE INVENTION

1. Field of the Invention

This invention pertains to an assay for the detection of levels of neutralizing antibodies effective against Infectious Bursal Disease Virus (IBDV) in poultry, specifically chickens. Particularly, a competitive ELISA is employed, using a labeled monoclonal antibody specific to all strains and serotypes of IBDV to determine a base line for the amount of this labeled antibody which will bind to a given amount of antigen (IBDV). The labeled antibody is admixed with the antigen and serum from the poultry, the reduced amount of binding between the labeled antibody and the antigen providing a reliable indication as to the amount of effective neutralizing antibody in the serum employed.

2. Background of the Prior Art

Infectious Bursal Disease Virus (IBDV) has been recognized as one of the principal economic drains on the poultry industry, responsible, alone, for the loss of extraordinarily high numbers of poultry individuals, and millions of dollars annually. In the disclosure of U.S. Patent Application 061,083, filed June 12, 1987, by Snyder et al, this problem, and the discovery of a monoclonal antibody specific to all known strains and serotypes of IBDV is disclosed in detail. Use of that monoclonal antibody (MCA) identified as R63 and expressed by the cell line deposited at the ATCC and bearing the Accession Number HB9490 and otherwise available from continuous viable cell lines maintained on the grounds of the University of Maryland, College Park campus, for conferring effective immunity against IBDV on new-born chicks is also disclosed in that application.

One problem widely encountered in the poultry industry in treating and preventing IBDV, whether it be through the use of MCA R63 or some other method, is identification of the level of antibody *effective* in neutralizing IBDV present in the serum of poultry individuals, and poultry flocks. A determination of the antibody level is necessary to determine the need for further immunization treatment, and the amount of treatment necessary, if appropriate.

Experience throughout the industry, and that of the inventor, indicates that the current method for determining antibody titer levels, an indirect-ELISA, does not give reliable results, the values obtained through this indirect assay and virus neutralization studies being, frequently, quite dissimilar.

It has been discovered that this lack of reproducability and reliability in results obtained through the currently marketed indirect-ELISA may be due to two significant factors associated with that assay. The current available assay measures not only antibodies effective in neutralizing IBDV (i.e., protective antibodies) but measures significant amounts of other antibodies which bind to the IBDV at non-neutralizing antigenic sites, and thus, gives a falsely high reading of antibody titer with respect to neutralization capacity of the serum. It should be noted that in the identified parent application of Snyder et al, it is disclosed that of the nine monoclonal antibodies developed in the study leading to the invention claimed therein, only two had any neutralizing effectiveness. Therefore, there are clearly non-neutralizing antigenic sites on the various strains of IBDV.

Currently available IBDV ELISA antibody kits also employ IBDV antigens that contain non-virus-related protein antigens which can be detected by probing with antisera monospecific to the suspect contaminants (e.g., fetal bovine serum bacterial antigens, fetal antigens contained in the serum, etc.). Antibodies which bind to these extraneous antigens are frequently present in the serum of vaccinated chickens and other poultry by virtue of vaccination with crude antigen preparations, and the binding of these antibodies is also measured falsely as anti-IBDV antibody in this indirect ELISA. Thus, currently available methods do not give reliable indications of the level of neutralizing, protective type IBDV antibody present in the serum of tested individuals.

SUMMARY OF THE INVENTION

This invention takes advantage of the fact that the previously disclosed monoclonal antibody R63 is specific to all known IBDV strains and serotypes, and "competes" only with itself and other antibodies recognizing the same neutralizing epitope present in chicken sera.

Thus, to give a reliable indication of IBDV neutralizing antibody titer in a poultry individual, a predetermined amount of labeled R63 is admixed with IBDV antigen and the serum from the poultry individual. The amount of labeled R63 binding to the IBDV is determined (through conventional methods employing the label, i.e., where the label is biotin, the amount of R63 unbound or bound is determined by admixing the appropriate supernatant or precipitate with an avidin-peroxidase complex (or the available substitute strep avidin) to which the biotin label will tightly bind). The amount of bound R63 is compared with a standard or base line, which is a measure of the amount of labeled R63 that binds in the absence of the serum of the poultry individual. The decrease in binding is due, directly, to the presence of neutralizing antibody present in the poultry individual serum, and accordingly, the decrease gives a reliable figure as to the level of neutralizing antibody present in the tested individual.

DETAILED DESCRIPTION OF THE INVENTION

General information concerning immunoassays, and ELISA specifically, is widely available to those of skill in the art, and this information and the methods by which such assays are prepared and conducted, do not constitute an inventive aspect of the subject matter addressed herein. Thus, those of skill in the art will be well familiar with the various methods of labeling antibodies, in order to perform competitive ELISA. As an exemplary label, biotin, which will subsequently tightly bind to the protein avidin, is mentioned. The biotin label is attached to the monoclonal antibody through well known methods. As much as 1 ml of "biotinylated" R63 preparation will yield 4000–16000 competitive ELISAs. Such a process is, therefore, clearly viable. As alternative labels or tags, many materials are known, such as radioactive iodine and radioactive cobalt, tritium, etc., any of a variety of enzymes, flourescing materials, etc. In various embodiments, the labeled antibody may be supported or unsupported. Preparative experimental work done in arriving at the invention disclosed and claimed herein employed a biotin labeled R63 monoclonal antibody.

The method of using the labeled antibody, in the competitive ELISA of the invention, is quite straight forward. The standard for a given amount of labeled R63 bound per unit of IBDV antigen may be determined, for any given batch, prior to dissemination to the user, or in conjunction with ease new assay run.

The labeled R63 is admixed, together with a predetermined amont of the IBDV antigen preparation corresponding to the amount employed at arriving at the standard and a sample of antibody-containing serum or plasma of the poultry individual to be tested, (e.g., poultry serum). The amount of labeled R63 bound to the antigen is determined, either by determining this directly, by determining amount of the bound material, by isolating and determining the amount of bound material, or indirectly, by determining the amount of unbound material left. This value obtained is compared with the standard previously established, and the difference is a measure of the presence of IBDV neutralizing antibodies present in the poultry individuals serum, which compete with the R63 for the effective binding site of the antigen. Actual tests conducted are set forth in the table attached hereto, which compares the results obtained from practicing the competitive ELISA of the claimed invention, the results obtained practicing the direct ELISA currently available, and virus neutralization tests, all for determining IBDV antibody titer in poultry individuals.

Obviously, numerous modifications and variations of the present invention are possible in light of the above teachings. It is therefore to be understood that within the scope of the appended claims, the invention may be practiced otherwise than as specifically described herein.

Comparison of C-ELISA, indirect ELISA,
and virus neutralization tests for
determining antibody titer to IBDV.

| Sample ID | C-ELISA[a,b] | ELISA[b,c] | VN Test[d,e] |
| --- | --- | --- | --- |
| NCS-0[f] | 1.093 | 0.000 | <10 |
| 1-0 | 0.164 | >1.500 | 204,800 |
| 2-2 | 0.184 | >1.500 | 102,400 |
| 3-4 | 0.262 | >1.500 | 51,200 |
| 4-8 | 0.383 | 1.410 | 12,800 |
| 5-32 | 0.603 | 0.756 | 3,200 |
| 6-64 | 0.696 | 0.351 | 800 |
| 7-128 | 0.826 | 0.312 | 400 |
| SPFY-0[g] | 1.095 | 0.595 | <10 |

[a]Average optical density at 450 nm.
[b]Background subtracted.
[c]Average optical density at 405 nm.
[d]100 TCID$_{50}$ virus was used.
[e]Neutralization titers are the reciprocal of a dilution.
[f]. . .-0 designates samples evaluated at a 1:500 dilution, . . .-2 designates samples diluted 1:2 and evaluated at 1:1000, . . .-8 was evaluated at a final dilution of 1:4000, and etc. by 2-fold.
[g]SPFY - a monospecific antiserum prepared against fetal bovine serum.

What is claimed as new and desired to be secured by Letters Patent of the U.S. is:

1. A method for determining the level of infectious bursal disease virus (IBDV) neutralizing antibody in poultry, comprising:
   A, admixing (1) a predetermined amount of labeled monoclonal antibody having the IBDV neutralizing capability of the monoclonal antibody expressed by hybridoma cell line ATCC-HB-9490, (2) infectious bursal disease virus antibody-containing fluid from said poultry, and (3) a predetermined amount of infectious bursal disease virus antigen;
   B, determining the amount of labeled monoclonal antibody not bound to said antigen in said admixing step, by measurement of the label attached to either said unbound monoclonal antibody or the label attached to monoclonal antibody bound to said antigen,
   C, comparing said amount of unbound labeled monoclonal antibody with a standard value for the amount of labeled monoclonal antibody remaining unbound in the absence of said poultry fluid as a measure of the level of IBDV neutralizing antibody in said fluid.

2. The method of claim 1, wherein said label is biotin.

3. The method of claim 1, wherein said amount of labeled monoclonal antibody not bound to said antigen in said admixing step is determined by detecting the label present in the complex formed by bound monoclonal antibody and said antigen.

4. The method of claim 1, wherein said amount of labeled monoclonal antibody not bound to said antigen is determined by detecting the label of said monoclonal antibody not bound during said admixing step.

5. The method of claim 2, wherein the presence of said label is detected by introducing an avidin-peroxidase complex to said biotin-labeled monoclonal antibody in the presence of a substrate which reacts to free peroxidase in a detectable manner.

6. The method of claim 5, wherein said reaction between said substrate and said peroxidase is detected optically.

7. A kit for conducting a competitive ELISA assay comprising, in separate containers, monoclonal antibody having the IBDV neutralizing capability of the monoclonal antibody expressed by hybridoma cell line ATCC HB-9490 bound to a label, and a predetermined amount of infectious bursal disease virus antigen.

8. The kit of claim 7, further comprising a container wherein said labeled antibody, said antigen and an amount of serum from poultry to be tested admixed.

9. The kit of claim 7, wherein said antibody is labeled with biotin.

* * * * *

UNITED STATES PATENT AND TRADEMARK OFFICE
CERTIFICATE OF CORRECTION

PATENT NO. : 4,908,305

DATED : March 13, 1990

INVENTOR(S) : David B. SNYDER

It is certified that error appears in the above-identified patent and that said Letters Patent is hereby corrected as shown below:

ON TITLE PAGE line [63], "June 12, 1987" should read --June 14, 1987--.

Column 4, line 65, after "tested", please insert --is--.

Signed and Sealed this

Twenty-third Day of June, 1992

Attest:

DOUGLAS B. COMER

*Attesting Officer*      *Acting Commissioner of Patents and Trademarks*